US007989001B2

(12) United States Patent
Kim et al.

(10) Patent No.: US 7,989,001 B2
(45) Date of Patent: Aug. 2, 2011

(54) METHOD OF SEPARATING TUMOR CELLS WITH AND WITHOUT LYMPHOTROPIC METASTATIC POTENTIAL IN A HUMAN CARCINOMA (76) Inventors: Untae Kim, Snyder, NY (US); Stefan A. Cohen, Tierra Verde, FL (US)

(*) Notice: Subject to any disclaimer, the term of this patent is extended or adjusted under 35 U.S.C. 154(b) by 1092 days.

(21) Appl. No.: 10/939,974

(22) Filed: Sep. 13, 2004

(65) Prior Publication Data

US 2006/0057588 A1 Mar. 16, 2006

(51) Int. Cl.
*A61K 35/12* (2006.01)
*A01K 67/00* (2006.01)
(52) U.S. Cl. .......................................... 424/573; 800/10
(58) Field of Classification Search .................. None
See application file for complete search history.

(56) References Cited

U.S. PATENT DOCUMENTS

| | | | |
|---|---|---|---|
| 5,399,493 A | 3/1995 | Emerson et al. |
| 5,536,642 A | 7/1996 | Barbera-Guillem et al. |
| 5,635,386 A | 6/1997 | Palsson et al. |
| 6,391,301 B1 | 5/2002 | Sleeman et al. |
| 6,667,034 B2 | 12/2003 | Palsson et al. |
| 6,790,604 B1 | 9/2004 | Cohen et al. |
| 2002/0119565 A1 | 8/2002 | Clarke et al. |
| 2003/0103938 A1 | 6/2003 | Jinquan et al. |
| 2003/0203416 A1 | 10/2003 | Staudt et al. |

OTHER PUBLICATIONS

Tian et al., Br J Cancer, 1999, 81: 814-821.*
Gorelik et al., Int J Cancer, 1982, 30: 107-112.*
Cohn et al., FEBS Lett, 1997, 403: 181-185.*
Griffiths et al., Clin. Cancer Res., 2003, 9: 6567-6571.*
Tanaka et al., Chest, 2003, 123: 1248-1253.*
B. Mueller et al, "Potential of the SCID Mouse as a Host for Human Tumors," Cancer and Metastasis Reviews, vol. 10, 1991, pp. 193-200.
R. Bankert et al, "Human-SCID Mouse Chimeric Models for the Evaluation of Anti-cancer Therapies," Trends in Immunology, vol. 22(7), 2001, pp. 386-393.
J. Fogh et al, "Analysis of Human Tumor Growth in Nude Mice," Proceedings of the Third International Workshop on Nude Mice, 1982, Gustav Fischer New York, pp. 447-456.
H. Klinger et al, "Modulation of the Activity of an Avian Gene Transferred into a Mammalian Cell by Cell Fusion," Proc. Nat. Acad. Sci. USA, vol. 71(4), 1974, pp. 1398-1402.
T. Kodama, "Pathology of Immunologic Regression of Tumor Metastases in the Lymph Nodes," GANN Monograph on Cancer Research, vol. 20, 1977, pp. 83-91.
R. Jirtle, "Blood Flow to Lymphatic Metastases in Conscious Rats," Europ. J. Cancer, vol. 17, 1981, pp. 53-60.
F. Wiener et al, "Fusion of Tumor Cells with Host Cells," Nature New Biology, vol. 238, 1972, pp. 155-159.
ATCC: Cell Biology Collection: Cell Biology Catalog (on line at www.atcc.org), ATCC No. CRL-1435, Designations: PC-3, 2005, pp. 1-3.
ATCC: Cell Biology Collection: Cell Biology Catalog (on line at www.atcc.org), ATCC No. CCL-227, Designations: SW620 [SW-620], 2005, pp. 1-3.
ATCC: Cell Biology Collection: Cell Biology Catalog (on line at www.atcc.org), ATCC No. HTB-26, Designations: MDA-MB-231, 2005, pp. 1-3.
ATCC: Cell Biology Collection: Cell Biology Catalog (on line at www.atcc.org), ATCC No. CCL-228, Designations: SW480 [SW-480], 2005, pp. 1-4.
F. Sharkey et al, "Metastasis of Human Tumors in Athymic Nude Mice," Int. J. Cancer, vol. 24, 1979, pp. 733-738.
S. Yano et al, "Novel Metastasis Model of Human Lung Cancer in SCID Mice Depleted of NK Cells," Int. J. Cancer, vol. 67, 1996, pp. 211-217.
G. Paine-Murrieta et al, "Human Tumor Models in the Severe Combined Immune Deficient (SCID) Mouse," Cancer Chemother Pharmacol, vol. 40, 1997, pp. 209-214.
A. Awad et al, "Dietary Phytosterol Inhibits the Growth and Metastasis of MDA-MB-231 Human Breast Cancer Cells in SCID Mice," Anticancer Research, vol. 20, 2000, pp. 821-824.
A. Awad et al, "In Vitro and in Vivo (SCID Mice) Effects of Phytosterols on the Growth and Dissemination of Human Prostate Cancer PC-3 Cells,"Eur J Cancer Prev,10, 2001,507-13.
T. Tanaka et al, "A Novel Monoclonal Antibody Against Murine IL-2 Receptor B-Chain," The Journal of Immunology, vol. 147(7), 1991, pp. 2222-2228.
J. Jonasson et al, "The Analysis of Malignancy by Cell Fusion. VII. ," J. Cell Science, vol. 24, 1977, pp. 217-254.
R. Cailleau et al, "Breast Tumor Cell Lines From Pleural Effusions," Journal of the National Cancer Institute, vol. 53(3), 1974, pp. 661-674.
M. Crespo et al, "ZAP-70 Expression as a Surrogate for Immunoglobulin-Variable-Region Mutations in Chronic Lymphocytic Leukemia," N Engl J Med, vol. 348, 2003, pp. 1764-1775.
Kim, U, "Pathogenesis and Characteristics of Spontanenously Metastasizing Mammary Carcinomas and the General Principles of Metastasis," J Surg Oncol, 1986, v. 33, pp. 151-165.
Kim, U. et al, "Differential Permeability of Lymphatic and Blood Vessels in Determining the Route of Metastasis as Demonstrated by Indirect Lymphography," Clinical Expl. Metastasis, 1988, vol. 6, pp. 291-299.

(Continued)

*Primary Examiner* — Ileana Popa
(74) *Attorney, Agent, or Firm* — James C. Simmons (57) ABSTRACT

A method for separating tumor cells with lymphotropic metastatic potential from those without lymphotropic metastatic potential in a human carcinoma. Cells of the carcinoma are transplanted in each of a plurality of fresh athymic mice. At least one of the athymic mice which does not develop a palpable tumor at the transplant site is treated to suppress the T-cell independent innate anti-tumor activity of natural killer cells therein. Tumor-forming cells at the transplant site of the treated athymic animal are harvested to obtain a cell line of cells with lymphotropic metastatic potential, which is also tested for the expression of T-lymphocyte associated molecules. Such cells are intimately associated with low or diminished angiogenicity and immunogenicity. The traditional scientific criteria for human cancer cells is re-defined, and therapeutic targets for human cancer cells is re-focused.

20 Claims, 5 Drawing Sheets

OTHER PUBLICATIONS

Goodison, S. et al, "Prolonged Dormancy and Site-specific Growth Potential of Cancer Cells Spontaneously Disseminated from Nonmetastatic Breast Tumors as Revealed by Labeling with Green Fluorescent Protein," Clin. Cancer Research, 2003, vol. 9, pp. 3808-3814.

Welch, D. et al, "Molecular Biology of Breast Cancer Metastasis. Genetic Regulation of Human Breast Carcinoma Metastasis," Breast Cancer Res., 2000, vol. 2, pp. 408-416.

Klein, C., "The Systemic Progression of Human Cancer. A Focus on the Individual Disseminated Cancer Cell—the Unit of Selection," Adv. Cancer Res., 2003, vol. 89, pp. 35-67.

Schmidt-Kittler, O. et al, "From Latent Disseminated Cells to Overt Metastasis: Genetic Analysis of Systemic Breast Cancer Progression," PNAC, 2003, vol. 100, pp. 7737-7742.

Kim, U. et al, "Immunologic Mechanisms of Selective Graft Resistance to Certain Malignant Tumors and Prevention of Metastases by Athymic Nude Mice," Proc. 3rd Int. Workshop on Nude Mice, Gustav Fischer New York, vol. 2, pp. 367-378.

Simon, R. et al, "Thymus-independent Host Resistance Against Growth and Metastases of Allogeneic and Xenogeneic tumors in Nude Mice," Proc. 3rd Int. Workshop on Nude Mice, Gustav Fischer New York, 1982, vol. 2, pp. 379-389.

Kim, U. et al, "Selective Suppression of T Cell Function in Normal Rats Simulating the T-Independent Antitumor and Antimetastatic Reaction of Nude Mice Against Metastasizing Carcinomas," Proc. 4th Int. Workshop on Immune-deficient Animals, Karger AG, Basel, Switzerland, 1982, pp. 235-238.

Tomita, N. et al, "Isolation and Characterization of a Highly Malignant Variant of the SW480 Human Colon Cancer Cell Line," Cancer Res., 1992, vol. 52, pp. 6840-6847.

Liang, L. et al, "Construction of a Metastasis-associated Gene Subtracted cDNA Library of Human Colorectal Carcinoma by Suppression Subtraction Hybridization," World J. Gastroenterology, 2004, vol. 10, pp. 1301-1305.

Hooper, J. et al, "Subtractive Immunization Using Highly Metastatic Human Tumor Cells Identifies SIMA 135/CDCP1, a 135 kDa Cell Surface Phosphorylated Glycoprotein Antigen," Oncogene, 2003, vol. 22, pp. 1783-1794.

Ticchioni, M. et al, "Signaling Through Zap-70 is Required for CXCL 12-mediated T-cell Transendothelial Migration," Blood, 2002, vol. 99, pp. 3111-3118.

Bosch, F. et al, "ZAP-70 Expression in Chronic Lymphocytic Leukemia: A New Parameter for an Old Disease," Haematologica, 2003, vol. 88, pp. 724-726.

Orchard, J. et al, "ZAP-70 Expression and Prognosis in Chronic Lymphocytic Leukemia," The Lancet, 2004, vol. 363, pp. 105-111.

Wiestner, A.et al, "Towards Molecular Diagnosis and Targeted Therapy of Lymphoid Malignancies," Semin. Hematol., 2003, vol. 40, pp. 296-307.

Durig, J. et al, "ZAP-70 Expression Is a Prognostic Factor in Chronic Lymphocytic Leukemia," Leukemia; 2003, vol. 17, pp. 2426-2434.

Crespo, M., "ZAP-70 Expression as a Surrogate for Immunoglobulin-variable-region Mutations in Chronic Lymphocytic Leukemia," N. Engl. J. Med., 2003, vol. 348, pp. 1764-1775.

Wiestner, A. et al, "Zap-70 Expression Identifies a Chronic Lymphocytic Leukemica Subtype with Unmutated Immunogolbulin Genes, Inferior Clinical Outcome, and Distinct Gene Expression Profile," Blood, 2003, vol. 101, pp. 4944-4951.

Liu, A., "Differential Expression of Cell Surface Molecules in Prostate Cancer Cells," Cancer Research, 2000, vol. 60, pp. 3429-3434.

Al-Hajj, M., "Prospective Identification of Tumorigenic Breast Cancer Cells," Proc. Natl. Acad. Science, 2003, vol. 100, pp. 3983-3988.

Kim, U. et al, "Resuscitation of the Non-tumorigenic, Natural Killer Cell (NK) Sensitive Clone of Human Prostate and Colon Cancer Cells in Nude Mice, and Comparison with Their Tumorigenic Counterpart: New Interpretation of Tumorigenicity," Abstract 4354, Proceedings of the American Association for Cancer Research, 1999, vol. 40, p. 660.

Kim, U. et al, "Critical Interrelationship Between Natural Killer Cells (NK) and B-cells in the Control of Growth and Metastasis of Human Breast Cancer as Manifested in Nude and SCID Mice, Abstract 1944, Proceedings of the American Association for Cancer Research," 2000, vol. 41. pp. 305-306.

Kim, U. et al, "Conversion of MMTV-induced Mouse Mammary Tumor (MTV) and EJ-ras Transformed NIH3T3 Sarcoma (3J1) Cell Lines into Highly Metastasizing Tumors by Fusion with Lymphoid Cells," Abstract 373, Proceedings of the American Association for Cancer Research, 1993, vol. 34, p. 63.

Kim, U. et al, "Immunological Escape Mechanism in Spontaneously Metastasizing Mammary Tumors, " Proc. Nat. Acad. Sci. USA, 1975, vol. 72, pp. 1012-1016.

Cohen, S. et al, "Capacity of Nonparenchymal Liver Cells To Control Metastasis," NK Cells in the Liver, 1995, R.G. Landes Co., Austin, TX, pp. 71-100.

Cohen, S. et al, "Role of Asialo-Gm1 Positive Liver Cells from Athymic Nude or Polyinosinic-polycytidylic Acid-treated Mice in Suppressing Colon-derived Experimental Hepatic Metastasis,"Cancer Research, 1990, vol. 50, pp. 1834-1840.

Ruoslahti, E., "How Cancer Spreads," Scientific American, Sep. 1996, pp. 72-77.

Yoon, W. et al, "Invasive and Metastatic, but Low Tumorigenic and Regressive Sub-clone of SW480 Human Colon Cancer Cells," Abstract 3638, Proceedings of the American Association for Cancer Research, 1997, vol. 38, p. 542.

Fidler, I., "Critical Factors in the Biology of Human Cancer Metastasis: Twenty-eighth G.H.A. Clowes Memorial Award Lecture," Cancer Research, 1990, vol. 50, pp. 6130-6137.

O'Reilly, M., "Angiostatin Induces and Sustains Dormancy of Human Primary Tumors in Mice," Nature Medicine, 1996, vol. 2, pp. 689-692.

Fidler, I. et al, "Metastasis Results from Preexisting Variant Cells Within a Malignant Tumor," Science, 1977, vol. 197, pp. 893-895.

Wang, N. et al, "Characterization of High- and Low-metastatic Clones Derived from a Methylcholanthrene-induced Murine Fibrosarcoma," Cancer Res., 1982, vol. 42, pp. 1046-1051.

Yefenof, E. et al, "Cancer Dormancy: Isolation and Characterization of Dormant Lymphoma Cells," Proc. Natl. Acad. Sci. USA, 1993, vol. 90, pp. 1829-1833.

Agarwal, D., "Expression of Matrix Metalloproteinase 8 (MMP-8) and Tyrosinase-related Protein-1 (TYRP-1) Correlates with the Absence of Metastasis in an Isogenic Human Breast Cancer Model," Differentiation, 2003, vol. 71, pp. 114-125.

Euer, N. et al, "Identification of Genes Associated with Metastasis of Mammary Carcinoma in Metastatic Versus Non-metastatic Cell Lines,"Anticancer Res, 2002, vol. 22, p. 733-40.

Schwirzke, M. et al, "Identification of Metastasis-associated Genes by Transcriptional Profiling of a Pair of Metastatic Versus Non-metastatic Human Mammary Carcinoma Cell Lines," Anticancer Research, 2001, vol. 21, pp. 1771-1776.

Montel, V. et al, "Altered Metastatic Behavior of Human Breast Cancer cells after Experimental Manipulation of Matrix Metalloproteinase 8 Gene Expression," Cancer Research, 2004, vol. 64, pp. 1687-1694.

Hayashi, K. et al, "Differential Effects of Retinoic Acid on the Growth of Isogenic Metastatic and Non-metastatic Breast Cancer Cell Lines and Their Association with Distinct Expression of Retinoic Acid Receptor Beta Isoforms 2 and 4," Int. J. Oncology, 2003, vol. 22, pp. 623-629.

Urquidi, V. et al, "Contrasting Expression of Thrombospondin-1 and osteopontin Correlates with Absence or Presence of Metastatic Phenotype in a Isogenic Model of Spontaneous Human Breast Cancer Metastasis," Clin. Cancer Res., 2002, vol. 8, pp. 61-74.

De Lange, R. et al, "Identification of Metastasis-associated genes by Transcriptional Profiling of Metastatic Versus Non-metastatic Colon Cancer Cell Lines," Anticancer Res., 2001, vol. 21, pp. 2329-2339.

Cailleau, R. et al, "Long-term Human Breast Carcinoma Cell Lines of Metastatic Origin: Preliminary Characterization," In Vitro, 1978, vol. 14, pp. 911-915.

Kim, U. et al, "New Approaches to the Control of Metastatic Breast and Colon Cancer: Focus on the T-Independent Selective Anti-tumor Immunity in Athymic Nude Mice," Abstract for AACR Annual Meeting, 1998, New Orleans, LA.

Kim, U. et al, "Manifestation of critical Interrelationship Between Natural Killer Cells (NK) and B-cells for the Control of Growth and Metastasis of Human Breast Cancer Xenografted in Nude and SCID Mice," Abstract 40089, American Society for Investigative Pathology, Experimental Biology, Mini-symposium on Breast Cancer, San Diego, CA, 2000.

Kim, U. et al, "Identification of Tumor Cells with Metastatic Potential and Control of their Growth by Manifestation of Innate Immunity: New Paradigm for Malignancy in Human Cancer," Abstract for Aegean Conferences: Innate Immunity Workshop, Santorini, Greece, 2000.

Kim, U. et al, "Innate Immunity Selectively Suppresses the Growth of Highly Invasive, Metastatic Human Cancer Cells, but helps Non-metastasizing Tumors to Grow and Metastasize to the Lung," Abstract 8018, presented at AAI Meeting, Orlando, FL, 2001.

Kim, U. et al, "Redefining Non-tumorigenic and Tumorigenic Cells Xenografted in Nude Mice: New Paradigm for Human Cancer, and Innovative Approaches for its Control," Abstract presented at MD Anderson's 56th Annual Symposium on Fundamental cancer Research—Cancer Immunity: Challenges for the Next Decade, Houston, TX, Oct. 14-17, 2003.

Kim, U. et al, "Manifestation of Lymphotropic Metastatic Potential and Expression of Terminal Deoxynucleotidyl Transferase Activities and T-lymphocyte Associated Antigens in Rat Mammary Tumor Cells Fused with Syngeneic Thymocytes," Abstract 265, Proceedings of the American Association for Cancer Research, 1988, vol. 29.

\* cited by examiner

METHOD OF SEPARATING TUMOR CELLS WITH AND WITHOUT LYMPHOTROPIC METASTATIC POTENTIAL IN A HUMAN CARCINOMA

The present invention relates generally to carcinomas, i.e., the malignant tumors of epithelial organs (including, but not limited to, breast, liver, lung, stomach, colon, and prostate gland). More particularly, the present invention relates to in vivo cloning of carcinoma cell lines. The present invention points to a new and promising paradigm for cancer research.

Unlike sarcomas (malignant tumors of mesenchymal origin, such as blood, connective tissue, bone, and cartilage), which spread directly to the lungs via the blood stream, carcinomas on the other hand usually metastasize first to the regional lymph nodes and then to distant organs; thus, metastasis of carcinomas is said to be normally lymphotropic. For most cancer cell types, the acquisition of metastasis generally leads to incurable disease. As discussed hereinafter, it is an object of the present invention to develop genetically identical matching pairs of carcinoma cell lines with and without lymphotropic metastatic potential respectively to be used for research (and perhaps other) purposes including the determination of molecular profiles of tumor cells with and without the intrinsic metastatic potential and the clinical estimation and prediction of relative invasiveness and metastasizing capacity in a tumor. Ultimately, it is hoped that this invention will lead to the development of new diagnostic as well as innovative treatment modalities (including new molecular targets therefor) for human carcinomas.

As discussed hereinafter, it is believed that much cancer research being conducted presently is on either human or laboratory animal cells which are generally non-metastatic. By developing carcinoma cell lines in accordance with the present invention which have lymphotropic metastatic potential, therefore research can then be conducted on cells which are known to have lymphotropic metastatic potential, and such cells are also found to be intimately associated with low or diminished angiogenicity and immunogenicity. It is of course also important to develop cell lines which do not have lymphotropic metastatic potential to serve as controls. See U. Kim et al, "Pathogenesis and Characteristics of Spontaneously Metastasizing Mammary Carcinomas and the General Principle of Metastasis," *J. Surgical Oncology,* 33:151-165, 1986, and cites 1, 2, and 23 therein by U. Kim et al; and U. Kim et al, "Differential Permeability of Lymphatic and Blood Vessels in Determining the Route of Metastasis as Demonstrated by Indirect Lymphography," *Clin. Expl. Metastasis,* 6:291-299, 1988. The author "U. Kim" in articles cited herein is one of the inventors of the present invention. By developing such cell lines in accordance with the present invention, a new and promising paradigm for human cancer research is thus opened up.

For many years, since Rygaard and Povlsen first successfully transplanted human colon carcinoma cells into the athymic nude mouse, cancer researchers have been using nude mice and other immune deficient laboratory animals as surrogate cancer patients for studying human cancer cells in vivo. See J. Rygaard et al, "Heterotransplantation of a Human Malignant Tumour to 'Nude' Mice," *Acta Path. Microbil. Scand.,* 77:758-760, 1969; B. Mueller et al, "Potential of the SCID Mouse as a Host for Human Tumors," *Cancer Metastasis Rev.,* 10:193-200, 1991; and R. Bankert et al, "Human-SCID Mouse Chimeric Models for the Evaluation of Anticancer Therapies," *Trends in Immunol.,* 22:386-393, 2001.

An "athymic" mouse or other animal, as used herein and in the claims, is defined as a mouse or other animal which is congenitally absent the thymus and thus unable to generate functional T lymphocytes. An athymic animal is normally also homozygous for the "nude" gene, hence nu/nu and no hair. Thus, the terms "nude" and "athymic" are used interchangeably herein. Usually cancer research is conducted on nude mice, but cancer research may be conducted on other nude animals such as, for example, nude rats or nude guinea pigs, though cancer research on such other animals is rare and costly.

Tumorigenic cells transplanted in nude mice may get pushed into the blood stream through defective endothelial cell junctions of blood vessels within large tumor mass and become trapped in the lung. See, for example, S. Goodison, "Prolonged Dormancy and Site-specific Growth Potential of Cancer Cells Spontaneously Disseminated from Nonmetastatic Breast Tumors as Revealed by Labeling with Green Fluorescent Protein," *Clin. Cancer Res.,* 9:3808-3814, Sep. 1, 2003. Such a form of blood-borne spread is called "passive tumor-cell embolization" and is not lymphotropic metastasis.

Unlike the successful xenograft (transplantation of tissues and cells from one species into a different species) of common laboratory animal tumors and normal tissues of diverse species, tumor biologists have found human carcinoma cells, especially the primary explants, to be difficult to grow in nude mice, their "take" rate ranging between 8.6% for breast, 12% for prostate, and 54% for colon cancer. See J. Fogh et al, "Analysis of Human Tumor Growth in Nude Mice," *Proc. 3rd Int. Workshop on Nude Mice,* 2, N. D. Reed (ed), Gustav Fischer: New York, pp. 447-456, 1982.

Despite the apparent inconsistency described above, researchers to this day have been using the "tumorigenicity" of transformed cells in nude mice together with their "anchorage-independent growth characteristics in vitro" as the principal scientific criteria for malignant phenotype. See S. Shin et al, "Tumorigenicity of Virus-transformed Cells in Nude Mice as correlated specifically with Anchorage independent Growth in Vitro," *Proc. Natl. Sci. USA,* 72:4435-4439, 1975.

For the purposes of this specification and the claims, the term "tumorigenic," or variants thereof, is meant to refer to the characteristic of cells, when transplanted in fresh athymic mice (or other athymic animals), as effecting the formation of a tumor at the transplantation site, and the term "non-tumorigenic," or variants thereof, is meant to refer to cells not having such a characteristic.

As discussed in the above S. Shin et al article as well as in D. Welch et al, "Molecular Biology of Breast Cancer Metastasis. Genetic Regulation of Human Breast Carcinoma Metastasis," *Breast Cancer Res.,* 2:408-416, 2000, tumorigenicity does not necessarily accompany metastasis, hence, tumorigenicity and metastasis cannot be used synonymously. C. Klein, "The Systemic Progression of Human Cancer. A Focus on the Individual Disseminated Cancer Cell—the Unit of Selection," *Adv. Cancer Res.,* 589:35-37, 2003, states that the direct molecular genetic characterization shows that dissemination occurs very early in the process of accumulation of genetic changes and suggests that metastasis may seldom be derived from the dominant clone of the primary tumor. Also see O. Schmidt-Kittler et al, "From Latent Disseminated Cells to Avert Metastasis. Genetic Analysis of Systemic Breast Cancer Progression," *Proc. Nat. Acad. Sci.,* 100:7737-7742, 2003, which also suggests that the proclivity or potential to metastasize is acquired early during multi-step tumorigenesis, thus also supporting the concept that tumorigenicity does not equate to metastasis.

In order to resolve the above inconsistency, a number of highly realistic, well characterized, non-immunogenic, spontaneously metastasizing rat mammary carcinomas (including TMT-081 and SMT-2A) in W/Fu female rats, resembling human breast cancer, and morphologically and growth-rate matched but non-metastasizing, immunogenic, chemically-induced mammary tumors in W/Fu female rats were systematically transplanted in nude mice of BALB/c, C3H, C57BL, or Swiss background, of both sexes. The metastasizing rat tumors were rejected or non-tumorigenic, while the non-metastasizing control tumors were accepted or tumorigenic and grew progressively. In this case, unlike previous research on animal tumors, the rat tumors behaved in nude mice similarly as human tumors behave in nude mice, and it is important to note that, like in human metastatic breast cancer, a cure has still not been found for these rat metastatic tumors. The same result was obtained even when the non-tumorigenic metastasizing and control non-metastasizing tumorigenic tumors were transplanted side-by-side in the same mouse, demonstrating that the T-cell independent innate immune system of a mouse could simultaneously distinguish one tumor from another. Such discriminatory microenvironments do not seem to be based on memory, for nude mice will reject subsequent challenges by either different or the same non-tumorigenic cells while still accepting tumorigenic ones. The serum of mice rejecting a tumor contained no tumor-specific antibody against the non-tumorigenic cells, indicating that the traditional function of T-cell mediated antibody production by B lymphocytes had no part in the rejection process. Thus, some other mechanism was involved in rejecting the tumor. Non-tumorigenic spontaneously metastasizing TMT-081 and SMT-2A tumors in nude mice could be temporarily revived for a short period by the suppression of T-cell independent innate anti-tumor activity including repeated injections of non-specific rabbit antiserum to nude mouse spleen cells or peripheral lymphocytes or by whole body irradiation. It was suspected that this revival activity may involve suppression of natural killer cells (NK). Specific anti-NK antibodies were more effective and highly selective for reviving and maintaining the growth of these tumor cells in nude mice. See the prior work of the present inventors and others in U. Kim, "Metastasizing Mammary Carcinomas in Rats: Induction and Study of Their Immunogenicity," *Science,* 167:72-74, 1970; U. Kim, "Pathogenesis of Spontaneously Metastasizing Mammary Carcinomas in Rats," *Gann Monogr.,* 20:73-81, 1977; U. Kim, "Pathogenesis and Characteristics of Spontaneously Metastasizing Mammary Carcinomas and the General Principle of Metastasis," *J. Surg. Oncol.,* 33:151-165, 1986; U. Kim et al, "Immunologic Mechanisms of Selective Graft Resistance to Certain Malignant Tumors and Prevention of Metastases in Athymic Nude Mice," *Proc. 3rd Int. Workshop on Nude Mice,* 2, N. Reed (ed), Gustav Fischer, New York, pp. 367-377, 1982; R. Simon et al, "Thymus-independent Host Resistance Against the Growth and metastasis of Allogeneic and Xenogeneic Tumors in Nude Mice," *Proc. 3rd Int. Workshop on Nude Mice,* N. D. Reed (ed), Gustav Fischer, New York, pp. 379-388, 1982; and U. Kim et al, "Selective Suppression of T Cell Function in Normal Rats. Simulating the T-independent Anti-tumor and Anti-metastatic Reaction of Nude Mice Against Metastasizing Rats Mammary Carcinomas," *Proc. 4th Int. Workshop on Immune-deficient Animals,* B. Sordat (ed), Karger A G, Basel, Switzerland, pp. 235-238, 1984. Biological, biochemical, and immunological characteristics of the metastasizing tumors (TMT-081, SMT-2A, and others) were compared with the non-metastasizing syngeneic rat mammary tumors (MT-100, MT-W9B, and others) matched according to their histological pattern and growth rate. With respect to their relative angiogenicity, the lymphotropic metastasizing tumors were found to have only one-fifth of the blood supply that the non-metastasizing control tumors had. U. Kim et al, "Differential Permeability of Lymphatic and Blood Vessels in Determining the Route of Metastasis as Demonstrated by Indirect Lymphography," *Clin. Expl. Metastasis,* 6:291-299, 1988; and R. Jirtle, "Blood Flow to Lymphatic Metastases in Conscious Rats," *European J. Cancer,* 17:53-60, 1981.

As previously discussed, it has been difficult to grow human carcinoma cells in nude mice. Even when tumor cells are first adapted to grow in vitro, their acceptance rate or tumorigenicity may increase, but such cells do not usually metastasize in the nude mouse (less than 1.7% metastasize) in the manner similar to their spread in their original patients, despite the fact that most tissue culture adapted human cancer cell lines are derived from metastatic lesions. See F. Sharkey et al, "Metastasis of Human Tumors in Athymic Nude Mice," *Int. J. Cancer,* 24:733-738, 1979, and *ATCC Catalogue of Cell Lines & Hybridomas,* 7th ed., pp. 248, 249, 255, and 270, 1992. This would suggest that either additional factors may be needed for achieving metastasis or the cells have qualitatively altered during the tissue culture process.

In order for NK-sensitive/non-tumorigenic cells in nude mice to grow and metastasize, the simultaneous suppression of NK and B cells seems to be necessary. This may be achieved by injections of rabbit antisera raised against nude mouse spleen cells and/or to peripheral lymphocytes or by treating SCID (severe combined immune deficient) mice implanted with the NK-sensitive cells with anti-NK antibody, as discussed in S. Yano et al, "Novel Metastasis Model of Human Lung Cancer in SCID Mice Depleted of NK Cells," *Int. J. Cancer,* 67:211-217, 1996; G. Paine-Murrieta et al, "Human Tumor Models in the Severe Combined Immunodeficient (scid) Mouse," *Cancer Chemother. Pharmacol.,* 40:209-214, 1997; A. Awad et al (including U. Kim), "Dietary Phytosterol Inhibits the Growth and Metastasis of MDA-MB-231 Human Breast Cancer Cells Grown in Nude Mice," *Anticancer Res.,* 20:821-824, 2000; and A. Awad et al (including U. Kim), "In Vitro and In Vivo (SCID Mice) Effects of Phytosterol on the Growth and Dissemination of Human Prostate Cancer PC-3 Cells," *Euro. J. Cancer Prevention,* 10:507-513, 2001. By "SCID" mouse or other animal, as the term is used herein and in the claims, is meant one which is deficient in both T and B lymphocytes.

During a series of xenograft studies of human tumor in nude mice (implanting about 2 million cells per mouse in the subcutaneous space of the right flank), it was noted that some of established human carcinoma cell lines derived from the American Type Culture Collection (ATCC) contained a mixture of tumorigenic and non-tumorigenic cell clones in varying proportions. Thus, among the five breast cancer cell lines tested, BT-20 and MCF-7 were fully tumorigenic (about 100%), MDA-MB-231 was partially tumorigenic (about 70%), and MDA-MB-157 and BT-474 were non-tumorigenic (about 0%). Among the three prostate cancer cell lines tested, PC-3 was partially tumorigenic (about 30%), LNCaP was minimally tumorigenic (about 5%), and DU-145 was non-tumorigenic (about 0%). Among the three colon cancer cell lines tested, HT-29 and SW620 were partially tumorigenic (about 33%) and SW480 was partially tumorigenic (about 70%). The SW480 cell line is from a primary (non-metastasized) cancer in a patient, and the SW620 cell line is from a secondary lesion in the same patient a year later after the patient developed lymph node metastasis, as discussed in our patent application cited hereinafter. The tumorigenicity of uncloned cell lines usually varies from laboratory to laboratory. When about 2 million tumor cells were implanted in each of nude mice, it usually took about 5 to 10 days for the tumorigenic breast cells to become palpable (tumor mass of about 5 mm or more in diameter, depending on the sensitivity of the person doing the palpating), about 2 to 5 weeks for the tumorigenic prostate cells, and about 7 to 14 days for the tumorigenic colon cells.

While athymic nude mice (as well as other athymic laboratory animals) are depleted of T lymphocytes, they still maintain functional natural killer cells (NK), macrophages, and B lymphocytes. In the absence of T-lymphocytes (as in the nude mouse), NK cells seem to become much more active. When the above non-tumorigenic cells were implanted in nude mice and the nude mice given mouse-specific anti-NK antibodies, tumors emerged at the implantation sites. The antibodies which were given were either the rabbit anti-AsialoGM1 antiserum (distributed by WAKO Chemicals, Inc. of Richmond, Va.), 25 microliter, injected i.p. (intraperitoneally) twice weekly for 4 to 5 weeks or longer or the rat TM-β1 monoclonal antibody (Mab) (see T. Tanaka et al, "A Novel Monoclonal Antibody Against MurineIL-2 Receptor B-chain: Characterization of Receptor Expression in Normal Lymphoid Cells and EL-4 Cells," *J. Immunol.*, 147:2222-2228, 1991), 100 microliter also given i.p. once when the non-tumorigenic cells were implanted and once again four weeks later. These observations seem to suggest that the NK-mediated T-cell independent anti-tumor mechanism involves the arrest of growth but not the killing of the target cells. When cells of a non-tumorigenic lymph node metastatizing SMT-2A rat mammary tumor, transplanted in nude mice and revived by an antibody to NK, were transplanted back into normal (fresh) syngeneic rats, the tumor grew promptly and manifested the typical lymph node metastasizing property of the original SMT-2A tumor, thus indicating that xenografted tumor cells grown in nude mice retain all of their original properties, including lymphotropic metastatic potential.

When non-metastasizing animal mammary and other solid tumor cells have been fused with syngeneic normal lymphoid cells, the hybrids not only acquired metastatic potential but also became structurally better differentiated or redifferentiated and had fewer chromosomes or assumed near diploid karyotypes. See F. Wiener et al, "Fusion of Tumour Cells with Host Cells," *Nature New Biol.*, 238:155-159, 1972; U. Kim, "Pathogenesis and Characteristics of Spontaneously Metastasizing Mammary Carcinomas and the General Principle of Metastasis," *J. Surg. Oncol.* 33:151-165, 1986; and J. Jonasson et al, "The Analysis of Malignancy by Cell Fusion. VII. Cytogenetic Analysis of Hybrids Between Malignant and Diploid Cells and Tumours Derived from them," *J. Cell Sci.*, 24:217-254 (1977).

A pair of less agressively growing and more agressively growing cell lines (SW480E and SW480R respectively) have been isolated from the human colon cancer cell line SW480, as discussed in N. Tomita et al, "Isolation and Characterization of a Highly Malignant Variant of the SW480 Human Colon Cancer Cell Line," *Cancer Res.*, 52:6840-6847, 1992. These SW480E and SW480R cell lines were isolated by eye-balling two distinct sub-populations of cells in the human colon cancer cell line SW480, one having a round morphology (SW480R), and the other having a epithelial morphology (SW480E) when grown in tissue culture. Thus, the pair of cell lines SW480E and SW480R were separated on the basis of their relative in vitro morphology (by eye-balling). This in vitro separation technique is thus not only very subjective but does not necessarily result in the separation of tumorigenic from non-tumorigenic cells. Thus, it is considered desirable to more reliably separate tumorigenic from non-tumorigenic cells.

Also, the Tomita et al article reported that when these separated cells (SW480E and SW480R) were thereafter grown in vivo in athymic nude mice by implanting them subcutaneously, the round cells (SW480R) were found to produce much larger tumors within the same time period than the epithelial ones (SW480E), even with a very high number of cells (5 million injected into 4 sites) in each SW480E inoculum. Tomita et al concluded that the SW480R phenotype is dominant over the SW480E phenotype.

Over the years, there have been many attempts to identify cellular and subcellular markers to distinguish tumor cells with and without metastatic potential. More recently, a technique known as suppressive subtractive hybridization has been used to construct a differentially-expressed gene subtracted cDNA library from the colorectal SW480 and SW620 cell lines (the same carcinoma before metastasis and after metastasis respectively, as previously discussed). See L. Liang et al, "Construction of a Metastasis-associated Gene Subtracted cDNA Library of Human Colorectal Carcinoma by Suppression Subtraction Hybridization," *World J. Gastroenterol.*, 10:1301-1305, 2004; and J. Hooper et al, "Subtractive Immunization Using Highly Metastatic Human Tumor Cells Identifies SIMA135/CDCP1, a 135 kDa Cell Surface Phosphorylated Glycoprotein Antigen," *Oncogene*, March, 2003. Also see U.S. Pat. No. 6,391,301 to Kim (one of the inventors of the present application) et al, the disclosure of which is incorporated herein by reference. Such a technique is not used to separate one cell line from another, but is instead used to search for markers in already separated cell clones or cell lines, i.e., to look for a marker in one cell line which is not in the other cell line.

As previously discussed, despite the fact that most human carcinoma cells are often non-tumorigenic and difficult to grow in tissue culture, representing the most critical property of transformed human carcinoma cells grown in nude mice, since the early 1980s researchers have been using the tumorigenicity of tumor cells in nude mice together with their anchorage-independent growth characteristics in vitro as the criteria for malignancy, thus ignoring the most important (non-tumorigenic) cell population in human cancer. Therefore, it seems that the tumorigenic cells upon which cancer researchers have performed many tests over many years seeking a cure for cancer may have limited significance or value. Since metastasis, the spreading property of cancer cells, is so deadly, it is important that when potential treatments for cancer are tested, the testing should be conducted on cells that are known to be malignant in human cancer patients.

Accordingly, it is an objective of the present invention to separate tumor cells with lymphotropic metastatic potential from those without such property in a human carcinoma so that potential new treatments for cancer can be tested on cells which are more realistic to human cancer.

In order to separate tumor cells with lymphotropic metastatic potential from tumor cells without lymphotropic metastatic potential in a human carcinoma, in accordance with the present invention, cells of the carcinoma are transplanted in each of a plurality of fresh athymic animals, at least one of the athymic animals which does not develop a palpable tumor at the transplant site is treated to suppress the anti-tumor activity of natural killer cells therein, and tumor-forming cells at the transplant site of the treated athymic animal are harvested to obtain a cell line of cells with lymphotropic metastatic potential.

The above and other objects, features, and advantages of the present invention will be apparent in the following detailed description of the preferred embodiment, when read in conjunction with the attached drawings wherein the same reference numerals depict the same or similar parts throughout the several views.

DETAILED DESCRIPTION OF THE PREFERRED EMBODIMENT

As discussed in our non-published co-pending application Ser. No. 09/110,376, filed May 12, 1998 now U.S. Pat. No. 6,790,604, issued Sep. 14, 2004), the disclosure of which is incorporated herein by reference, it is believed (but without wishing to be bound by theory here or elsewhere in this specification) that a carcinoma may comprise a sub-population of cells which have lymphotropic metastatic potential and a sub-population of cells which do not have lymphotropic metastatic potential. Also see U.S. Pat. No. 5,536,642 to Cohen (one of the inventors of the present invention) et al, the disclosure of which is also incorporated herein by reference. It is also believed that the above discussion indicates that NK-sensitive cells in nude mice possess the lymphotropic metastatic potential and that the NK-resistant cells do not.

In this specification and the claims, cells are said to be NK-resistant (nkR) when they form palpable tumors that will grow progressively in athymic animals (or otherwise T-lymphocyte deficient environment which is permissive to such growth) which have a normal amount of NK (natural killer) cells and their products (or otherwise T-lymphocyte independent innate anti-tumor immunological milleau) and the effects of which NK cells and products or milleau are not suppressed, and cells are said to be NK-sensitive (nkS) when their growth is suppressed or arrested, i.e., they do not form palpable tumors in such NK-normal athymic animals or environment. NK cells are normally specific to the animal in which they are born and reside, i.e., athymic mice normally contain mouse-specific NK cells. As used in this specification and the claims, the term "natural killer cells" or "NK cells" is defined as defined in W. Herbert et al (eds), The Dictionary of Immunology, Academic Press, 1995, and is meant to include any other cells and/or their products which are equivalent to natural killer cells and/or their products in the sense that they likewise have the effect of suppressing tumor growth of NK-sensitive cells in situ. NK cells are cytotoxic lymphocytes which lack the phenotypic markers of both T-cells (TCR, CD3) and B-cells (membrane immunoglobulin). They bear CD16 and CD56 as characteristic markers. They contain prominent cytoplasmic granules and are morphologically distinguishable as "large granular lymphocytes," and the granules contain granzymes and the cells release performs which are inserted into the membranes of target cells. Activated NK cells make various cytokines. A heterodimeric cytokine IL-12 activates NK as well as T cells. The products of NK cells include, but are not limited to, interferon (INF) gamma, CD95L, and CD154 (ligand of CD40).

Figure 1A:
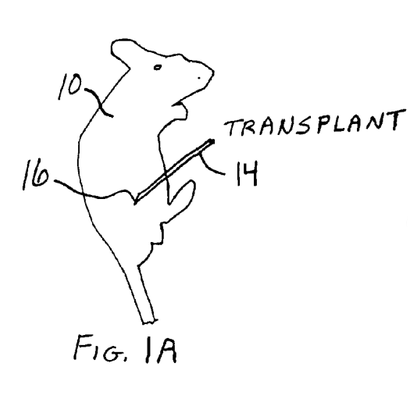
FIGS. 1A and 1B are schematic views of cells of a human carcinoma being transplanted into respective athymic mice.

Referring to FIGS. 1A through 4, there is illustrated chronologically a process, in accordance with the present invention, for separating tumor cells with lymphotropic metastatic potential from tumor cells without lymphotropic metastatic potential in a single human carcinoma. Thus, a method is illustrated for forming from the single human carcinoma a pair of genetically identical or isogenic cell line clones. In accordance with the process, the NK-sensitive or non-tumorigenic cells (which are believed to possess the lymphotropic metastatic potential) are separated from the NK-resistant or tumorigenic cells (which are believed not to possess the lymphotropic metastatic potential). FIGS. 1A and 2A illustrate the chronological progression of a first fresh athymic nude mouse 10 while FIGS. 1B, 2B, 3, and 4 illustrate the chronological progression of a second fresh athymic nude mouse 12. It should be understood that the method should normally utilize a plurality of mouse 10 and a plurality of mouse 12.

For the purposes of this specification and the claims, the term "fresh," when referring to athymic animals, is meant to refer to an athymic mouse or other athymic animal (normally young adult, whose innate T-cell independent immune system is still active) on which no prior experimentation or treatment has been conducted, except for de minimus experimentation or treatment which would not affect the outcome of the conducting of the process of the present invention, it being understood that the mouse or other animal will be sufficiently normal for performance suitably of the process of the present invention thereon.

Figure 1B:
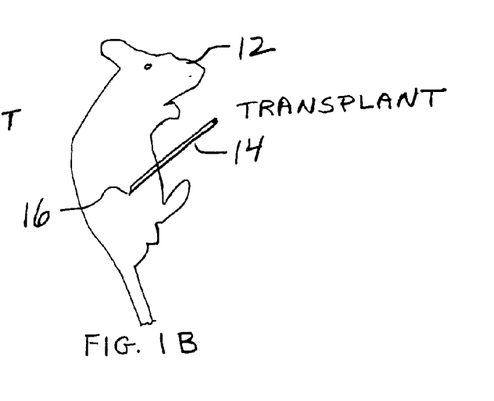

FIGS. 1A and 1B illustrate the initiation of the process wherein a standardized number of single cell preparations from the same human carcinoma are xenografted or transplanted into each of the mice 10 and 12 respectively, for example, by means of a hypodermic syringe with a small gauge needle 14, which may, for example, be 25 gauge, inserted subcutaneously into a flank of the mouse at site 16, which may, for example, be a young adult of one to two months old. While only two mice are shown, it should be understood that in practice a number of such mice, for example, ten mice, may be used for the process, the greater the number of mice used the better the results should be, and hence improving the chances of successfully separating with sufficient purity the non-tumorigenic cells from the tumorigenic ones. Each of the mice 10 and 12 may be transplanted with a standardized number of fresh viable cell suspensions, for example, about 2 million cells/mouse, given in, for example, a 0.1 ml suspension.

Figure 2A:
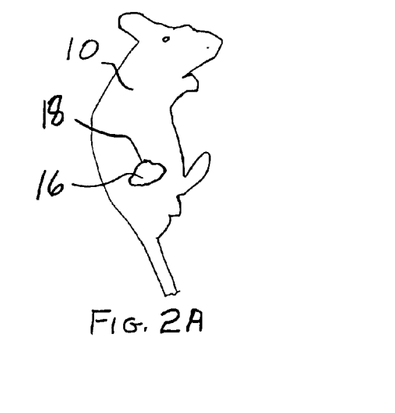
FIGS. 2A and 2B are schematic views of the mice of FIGS. 1A and 1B respectively one to three weeks after the transplantation.
Figure 2B:
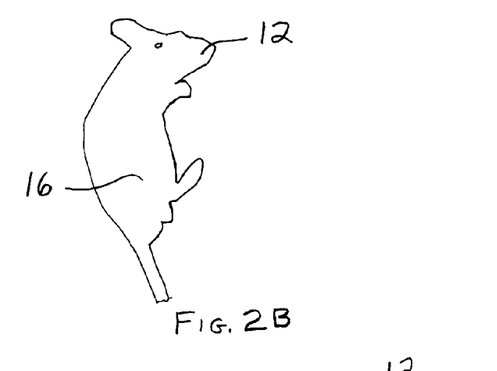

FIGS. 2A and 2B illustrate the mice 10 and 12 respectively alter about a week has passed since the transplantation illustrated in FIGS. 1A and 1B. As seen therein, a palpable tumor mass, illustrated at 18, has developed at the site 16 of injection in mouse 10. No tumor mass is seen in mouse 12 at this time. Since mouse 10 has not been depleted of NK cells, this means that the progressively growing cells in tumor mass 10, which are tumorigenic, are resistant to NK cells and therefore lack lymphotropic metastatic potential, with the possible exception that there may be some NK-sensitive cells mixed in with the NK-resistant cells. Mouse 10 is selected, and, when tumor 18 has grown to a manageable size, for example, about 1 cm in diameter, cells in the tumor mass 18 are harvested, i.e., surgically removed aseptically in accordance with principles commonly known to those of ordinary skill in the art to which this invention pertains, to establish a first cell line, as discussed hereinafter, of a sub-population of tumorigenic, cells, which, as discussed herein, are considered to be cells without lymphotropic metastatic potential. If it is not desired that such a cell line be established, then mouse 10 may he discarded without harvesting the cells in tumor 18. On the other hand, if it is not desired that a sub-population of cells with lymphotropic metastatic potential be established, then mouse 12 may be discarded at this time. The discussion hereafter is based on the assumption that it is desired to establish both cell lines.

Mouse 12 preferably should be watched for an additional length of time, for example, for breast cancer wherein a palpable tumor is expected to show up within about 5 to 10 days, until at least about 2 weeks after the transplantation to allow the development of a palpable tumor by tumorigenic cells, preferably at least about 3 weeks after the transplantation to allow time for even slow growing tumorigenic cells to develop a palpable tumor mass. The length of time may vary with different cancer cells. For another example, for prostate cancer wherein a palpable tumor is expected to not show up until about 2 to 5 weeks after transplantation, the additional length of time that mouse 12 should be watched is desirably until at least about 6 or more weeks after the transplantation. If no palpable tumor mass is observed after the requisite period of time, then mouse 12 may be suspected of harboring non-tumorigenic cells. In accordance with the present invention, palpable tumor nodule-free mouse 12 is treated, as described in greater detail hereinafter, to suppress anti-tumor activity thereof, i.e., to deplete the mouse 12 of mouse-specific natural killer (NK) cells and/or their products or to otherwise suppress effects thereof, particularly the effect of suppressing or arresting tumor growth of NK-sensitive cells in situ.

Figures 3, 4:
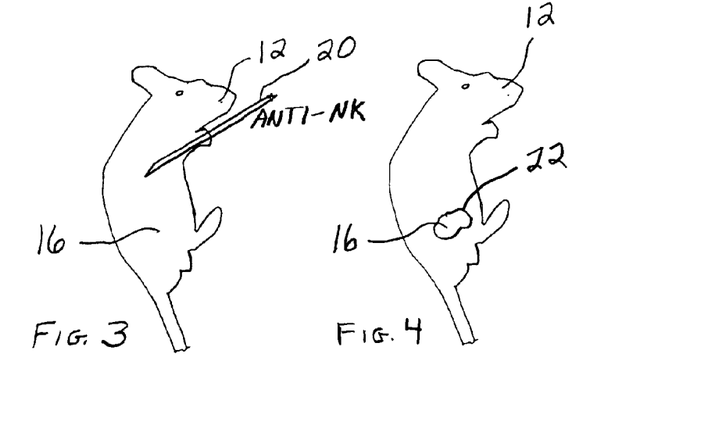
FIG. 3 is a schematic view of the mouse of FIGS. 1B and 2B being injected with anti-NK antibodies three weeks after the transplantation.
FIG. 4 is a schematic view of the mouse of FIGS. 1B, 2B, and 3 four weeks after the transplantation.

As illustrated in FIG. 3, in order to suppress anti-tumor activity, in accordance with the present invention, palpable tumor nodule-free mouse 12 is then injected intraperitoneally, as illustrated by needle 20, with an anti-mouse natural killer (NK) cell antibody, which may be polyclonal or monoclonal, repeatedly at regular intervals, for example, every 3 to 6 days, until a tumor appears at the original transplantation site, as illustrated in FIG. 4 by the appearance of tumor 22. When tumor 22 has grown to a manageable size, for example, about 1 cm in diameter, cells in the tumor mass 22 are harvested, similarly as for tumor mass 18, to establish a second cell line, as discussed hereinafter, of a sub-population of cells with lymphotropic metastatic potential.

While separate groups of cells with and without lymphotropic metastatic potential have now been obtained and can now be used in research, it is considered desirable to place such groups of cells in a more desired condition (cultivated) for research and to purify to a desired purity or homogenity and confirm the purity or homogenity of the cell lines, i.e., to remove any tumorigenic cells mixed in with the non-tumorigenic cells and to remove any non-tumorigenic cells mixed in with the tumorigenic cells. In order to develop cultivated cell lines of a desired purity, in accordance with a preferred embodiment of the present invention, single-cell suspensions are prepared from each solid tumor mass 18 and 22, and the tumorigenic and the antibody revived non-tumorigenic cells from tumor masses 18 and 22 are cultivated separately in tissue culture, using procedures commonly known to those of ordinary skill in the art to which the present invention pertains.

Cells of each of the tissue-cultured cell lines are implanted back subcutaneously into fresh intact normal athymic nude mice respectively similarly as cells of the explanted carcinoma were transplanted into nude mice. The growth of the in vivo implanted cells is observed to confirm the status of the implanted tumorigenic cells as being tumorigenic and the status of the implanted non-tumorigenic cells in a separate fresh nude mouse as being non-tumorigenic. A fresh group of tumorigenic cells are harvested, similarly as described with reference to FIGS. 1A and 2A and again cultured in vitro to obtain a more pure cell line. Likewise, a fresh group of non-tumorigenic cells are harvested, similarly as described with reference to FIGS. 1B, 2B, 3, and 4 and again cultured in vitro to obtain a more pure cell line. The above-described in vivo and in vitro cycles of cell line development are preferably repeated as many times, for example, at least three or more times, to insure that the tumorigenic and non-tumorigenic cells are clearly separated and that each group of cells has a cell population of a desired purity.

Using the process of the present invention as described with reference to FIGS. 1 to 4, we have isolated three sets of genetically identical matching pairs of sub-populations or clones from human cancer cells. Thus, from the human breast cancer cell line MDA-MB-231 (see R. Cailleau et al, "Breast Tumor Cell Lines from Pleural Effusions," *J. Natl. Cancer Inst.*, 53:661-674, 1974), we isolated a pair of clones MB-231/nkS (NK sensitive) and MB-231/nkR (NK resistant). From the human prostate cancer cell line PC-3 (see M. Kaighn et al, "Establishment and Characterization of a Human Prostatic Carcinoma Cell Line (PC-3)," *Invest. Urol.*, 17:16-23, 1979), we isolated a pair of clones PC-3/nkS (NK sensitive) and PC-3/nkR (NK resistant). From the human colon cancer cell line SW480 (see the aforesaid N. Tomita et al article), we isolated a pair of clones SW480/nkS (NK sensitive) and SW480/nkR (NK resistant).

Figure 5:
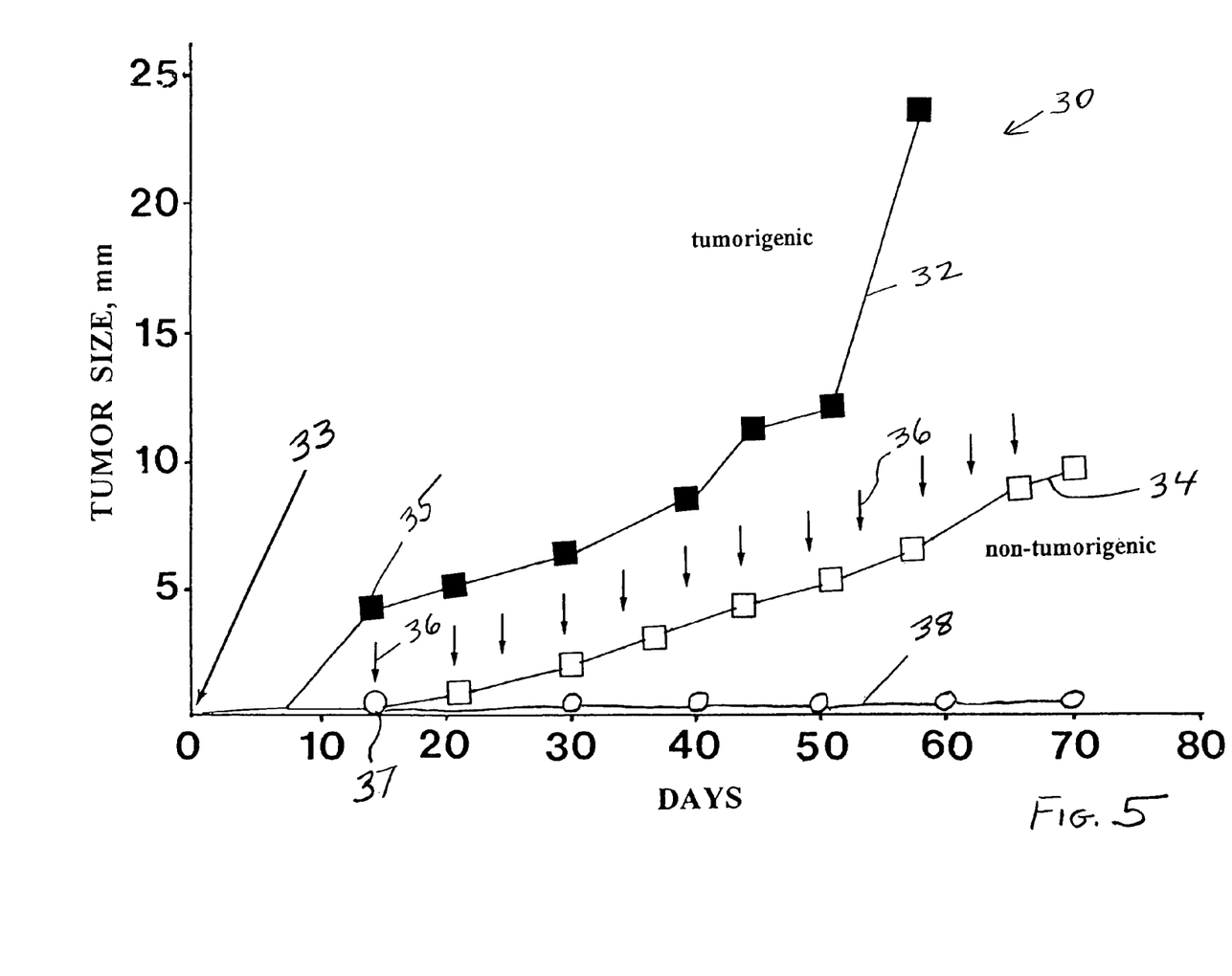
FIG. 5 is a graph of tumor size over time (days) of tumorigenic (MB-231/nkR) and non-tumorigenic (MB-231/nkS) human breast carcinoma cells from the cell line MDA-MB-231 xenografted in athymic nude mice, illustrating the separation and establishment of the MB-231/nkR (NK-resistant) and MB-231/nkS (NK-sensitive) clones from the cell line.

Referring to FIG. 5, there is shown generally at 30 a graph of the growth characteristics of tumorigenic (MB-231/nkR) and non-tumorigenic (MB-231/nkS) sub-populations 32 and 34 respectively of human breast cancer MDA-MB-231 cells xenografted (transplanted) in athymic nude mice using the process described with respect to FIGS. 1A to 4, transplantation of the cancer cells in the mice (about 2 million cells per mouse) occurring at the beginning of the experiment, as indicated at 33. As seen in FIG. 5, the tumorigenic clone or sub-population 32 grew to a tumor size of about 4 to 5 mm (thus palpable) within about 2 weeks, as indicated at 35, while there is still no indication of the non-tumorigenic clone or sub-population 34. For the suppression of NK activity in the mice showing no palpable signs of tumor after 2 weeks, these mice were repeatedly injected with anti-mouse NK anti-serum, in accordance with the process described with reference to FIG. 3, as illustrated by arrows 36, the first injection being at about 2 weeks after transplantation and being administered about every 4 to 6 days. The anti-NK serum used was the rabbit AsialoGM1 antiserum and the TM-β1 rat Mab used interchangeably at a dosage of 25 microliter of the antiserum, injected i.p. (intraperitoneally), per mouse. The tumor size represents an average diameter of about 4 to 6 tumors, selected randomly, from each respective group (those having tumorigenic cells and those not having tumorigenic cells) of mice. A third group of mice (a sub-set of the mice having non-tumorigenic cell sub-populations), which did not have palpable tumors but which were not injected with anti-NK serum, remained palpable tumor-free during the duration of the experiment, as indicated at 38. It can be seen in FIG. 5 that, after injections of the anti-NK serum began, a tumor of the non-tumorigenic cells began to form, became palpable, and continued to grow with the repeated injections 36.

Figure 6:
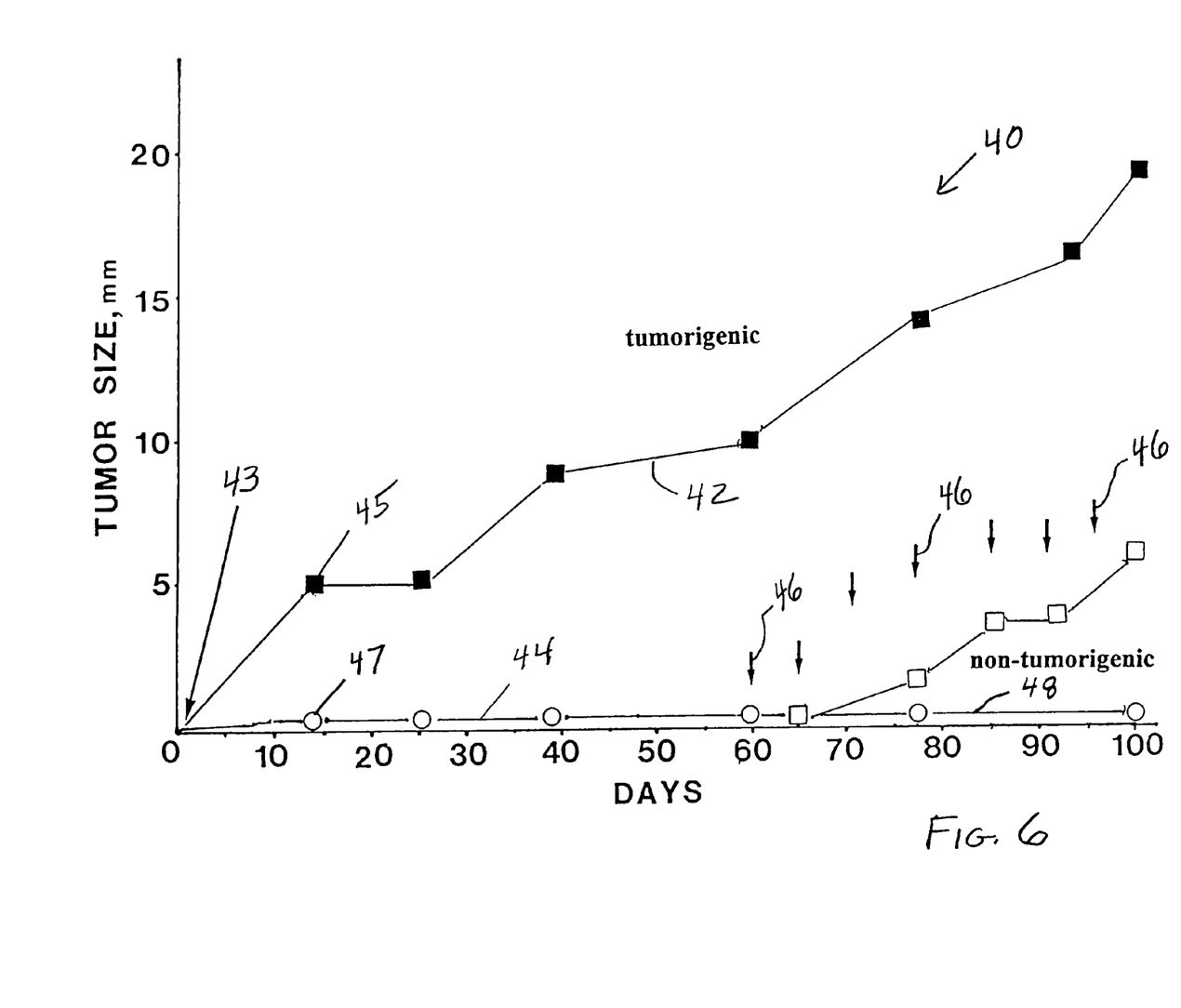
FIG. 6 is a graph similar to that of FIG. 5 for the human prostate carcinoma cell line PC-3, illustrating the separation and establishment of the NK-resistant (PC-3/nkR) and NK-sensitive (PC-3/nkS) clones from the cell line.

Referring to FIG. 6, there is shown generally at 40 a graph of the growth characteristics of tumorigenic (PC-3/nkR) and non-tumorigenic (PC-3/nkS) sub-populations 42 and 44 respectively of the human prostate carcinoma cell line PC-3 xenografted (transplanted) in athymic nude mice using the process described with respect to FIGS. 1A through 4, transplantation of the cancer cells in the mice (about 2 million cells per mouse) occurring at the beginning of the experiment, as indicated at 43. As seen in FIG. 6, the tumorigenic clone or sub-population 32 grew to a tumor size of about 5 mm (thus palpable) within about 2 weeks, as indicated at 45, while there is still no indication of the non-tumorigenic clone or sub-population 44, as indicated at 47. In fact, the non-tumorigenic cell sub-population remained dormant (no palpable tumors) for 60 days before treatment began with anti-NK serum while the tumorigenic sub-population 42 continued to grow. For the suppression of NK activity in the mice showing no palpable signs of tumor after 60 days, these mice were repeatedly injected with anti-mouse NK serum, in accordance with the process described with reference to FIG. 3, as illustrated by arrows 46, the first injection being at about 60 days after transplantation and being administered about every 5 days. The anti-NK serum used was rabbit anti-mouse AsialoGM1 or rat anti-mouse monoclonal antibody TMβ1 used interchangeably at a dosage of about 25 microliter of the antiserum, injected i.p. (intraperitoneally), per mouse. The tumor size represents an average diameter of about 4 to 6 tumors, selected randomly, from each respective group (those having tumorigenic cells and those not having tumorigenic cells) of mice. A third group of mice (a sub-set of the mice having non-tumorigenic cell sub-populations), which did not have palpable tumors but which were not injected with anti-NK serum, remained palpable tumor-free during the duration of the experiment, as indicated at 48. It can be seen in FIG. 6 that, after injections of the anti-NK serum began, a tumor of the non-tumorigenic cells began to form, became palpable, and continued to grow with the repeated injections 46.

Figure 7:
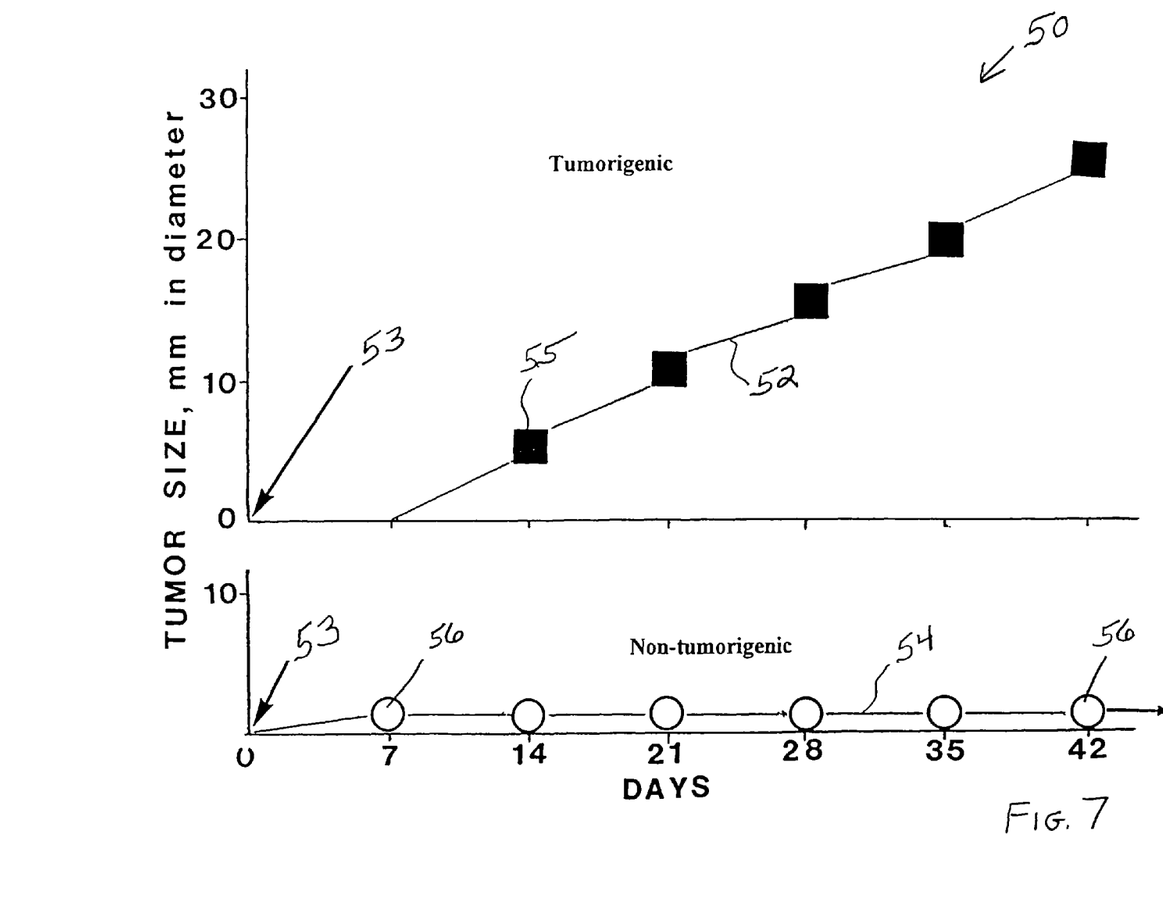
FIG. 7 is a graph similar to that of FIG. 5 for the human colon carcinoma cell line SW480, illustrating the separation and establishment of the NK-resistant (SW480/nkR) and NK-sensitive (SW480/nkS) clones from the cell line.

Referring to FIG. 7, there is shown generally at 50 a graph of the growth characteristics of tumorigenic (SW480/nkR) and non-tumorigenic (SW480/nkS) sub-populations 52 and 54 respectively of the human colon carcinoma SW480 cells xenografted (transplanted) in athymic nude mice using the process described with respect to FIGS. 1A through 4, transplantation of the cancer cells in the mice (about 2 million cells per mouse) occurring at the beginning of the experiment, as indicated at 53. As seen in FIG. 7, the tumorigenic clone or sub-population 52 grew to a tumor size of about 4 to 5 mm (thus palpable) within about 2 weeks, as indicated at 55, while there remains throughout the duration of the experiment no indication of the non-tumorigenic clone or sub-population 54, as indicated at 56, for one group of mice with the non-tumorigenic sub-population. The tumor size represents an average diameter of about 4 to 6 tumors, selected randomly, from the mice bearing the tumorigenic cells.

Figure 8:
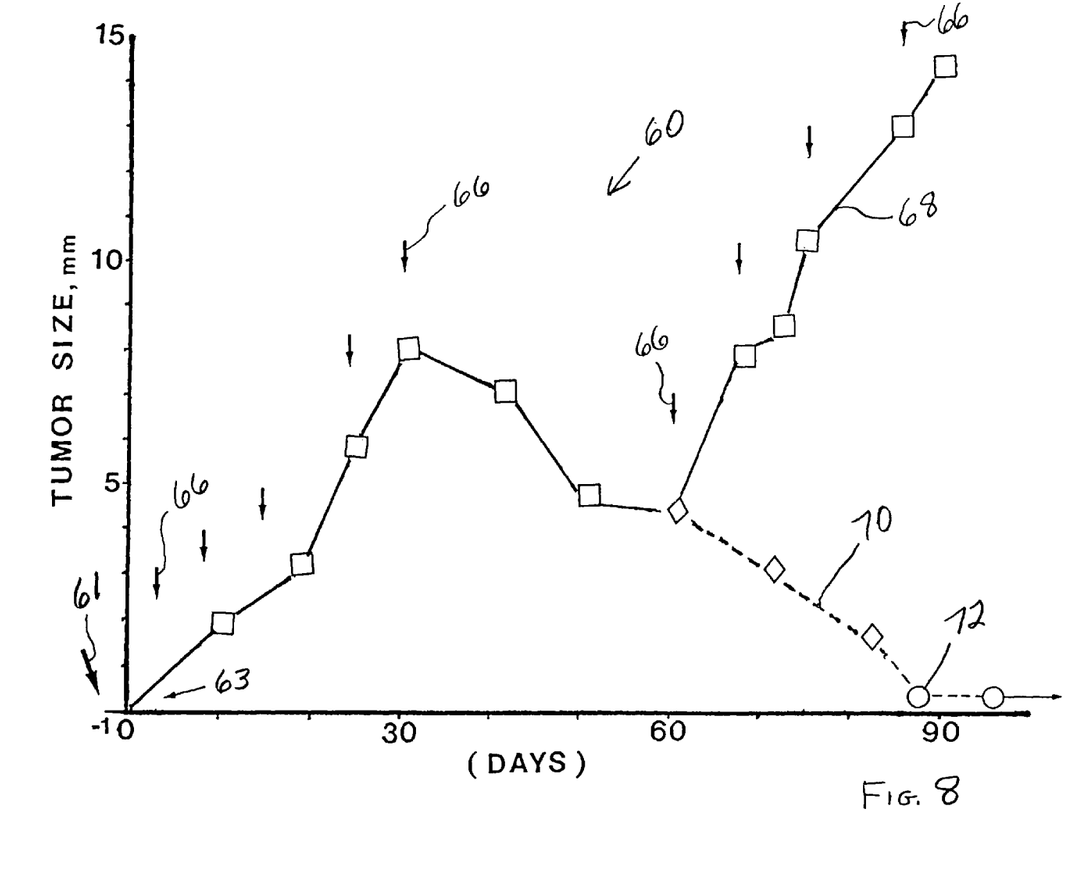
FIG. 8 is a graph of tumor size over time (days) illustrating the growth and non-growth of NK-sensitive SW480/nkS cells with and without anti-NK treatment respectively thereof.

Referring to FIG. 8, there is shown generally at 60 a graph of the growth characteristics of well-established non-tumorigenic NK-sensitive SW480/nkS cells in athymic nude mice (6 BALB/c athymic nude mice each transplanted with about 2 million NK-sensitive SW480/nkS cells), as indicated at 61. For the suppression of NK activity in the mice, these mice were repeatedly injected beginning two days after the transplantation 61 (as indicated at 63) with anti-mouse NK serum, in accordance with the process described with reference to FIG. 3, as illustrated by arrows 66, the injections 66 being administered a total of 6 times spaced over the first 30 days of the experiment. As seen in FIG. 8, the non-tumorigenic cells began immediately to grow and continued to grow throughout this 30-day period during which the anti-mouse NK serum was repeatedly administered to the mice, reaching a tumor size of about 8 mm. As also seen in FIG. 8, there was no anti-mouse NK serum administered to the mice during the second 30-day period (between days 30 and 60), and the tumor size is shown to decrease or regress (shrank by about 50%) during this period. At 60 days, the mice were divided into two groups, those for whom the anti-mouse NK serum treatment was resumed, illustrated at 68, and those who were continued to be left untreated with the anti-mouse NK serum for the remainder of the experiment. As seen in FIG. 8, those receiving anti-mouse NK serum (4 times spaced) during the last 30 days (between days 60 and 90) had increases in tumor size (nearly tripled in tumor size to about 14 mm), while the mice not treated with anti-mouse NK serum during this period continued to have decreases in tumor size, and their tumors disappeared (perhaps becoming dormant again) by the end of the 90 days, as indicated at 72. The untreated mice were monitored for two additional months, and their tumors never returned. The anti-NK serum used was the anti-AsialoGM1 antibody at a dosage of about 25 microliter of the antiserum, injected i.p. (intraperitoneally), per mouse. The tumor size represents an average diameter of about 4 to 6 tumors, selected randomly. Graph 60 (FIG. 8) thus shows the complete dependence of the NK-sensitive cells on sustained suppression of NK activity in athymic nude hosts.

The experiments illustrated in FIGS. 5 through 8 show that a carcinoma may have two (or more) sub-populations of cells, one which is resistant to NK cells in athymic nude mouse and which are therefore tumorigenic and grow at the site of transplantation, and another sub-population of cells which are sensitive to NK cells in athymic mude mice and are caused by the host NK cells to be dormant or growth-suppressed therein but which can be revived to form palpable tumors when the athymic mude mice in which they are transplanted are treated with anti-NK serum. The revival of NK-sensitive cells (which, as discussed hereinafter, are believed to have metastatic potential) after a prolonged dormancy may interestingly be compared to the recurrence of aggressive cancer seen in human cancer patients after a long remission.

By increasing the number of NK-sensitive (non-tumorigenic) cells by double or triple or more (4 to 6 million cells per inoculum), the innate immunity of nude mice may be overwhelmed, which may result in the non-tumorigenic cells being accepted (rendered tumor-forming) temporarily. It was observed that the resulting tumors did not grow larger than about 5 mm in diameter and that, when left alone, the tumors disappeared completely within about a month. It may thus be concluded that the availability of NK cell pools in normal nude mice at a given time may be limited, requiring replenishment of NK cells to meet a greater tumor challenge. Thus, the number of cells per inoculum is preferably limited to a number which does not overwhelm the mouse's or other animal's NK cells. The number of cells is preferably large enough so as not to require waiting indefinitely for tumors to appear. For example, for performance of the method of the present invention in a nude mouse, an inoculum which contains about 2 million cells seems to be optimal.

Interestingly, the anti-NK antibody revived human or rat tumor cells actively growing in NK-depleted nude hosts still failed to manifest their lymph node metastasizing capacity, indicating a possible role of B lymphocytes and other factors for preventing the expression of metastatic potential by NK-sensitive cells in a T-cell deficient environment.

As discussed in greater detail in our aforesaid patent application, in order to relate the phenotypic characteristics of NK-sensitive inherently metastasizing and NK-resistant non-metastatic tumor cells to the expression of lymphoid specific genes including Vβ genes along with related TCR associated surface and signal transduction genes in these tumor cells, differential expressions of a number of cell markers have been analyzed. Thus, certain lymphoid gene products (markers) including, but not limited to, CD3, CD4, CD8, ZAP-70, and SYKB were found in much greater abundance on metastasizing tumors (or cell lines) than on non-metastasizing tumors (or cell lines).

As discussed hereinafter, biochemical marker analysis was done with tumor cells derived from the SW480E and SW480R cells originated in the Tomita et al laboratory. However, when these cells were subjected to the relative tumorigenicity test in athymic nude mice in accordance with the present invention, the SW480E cells were found to be non-tumorigenic, NK-sensitive, and hence revivable by the specific anti-mouse NK cell treatment, while the SW480R cells were tumorigenic and NK-resistant. Thus, with respect to their relative NK-sensitivity, the morphologically separated cell lines (SW480R and SW480E of Tomita et al) seem to be indistinguishable from the matching pairs of in vivo cloned cells in nude mice (the non-tumorigenic and NK-sensitive SW480/nkS and the tumorigenic and NK-resistant SW480/nkR respectively) that were separated by us from the parental cell line SW480 using the in vivo cloning procedure of the present invention. Furthermore, judging from the previously discussed demonstration of non-tumorigenicity and NK-sensitivity by the spontaneously metastasizing rat mammary tumors and the tumorigenicity and NK-resistance by the non-metastasizing control rat mammary tumors in nude mouse xenograph studies, the non-tumorigenicity and NK-sensitivity of human cancer cells may be intimately be associated with lymphotropic metastatic potential and the tumorigenic cells may be without lymphotropic metastatic potential.

The role of ZAP-70, a tyrosine kinase normally expressed in T and NK cells, is discussed in M. Ticchioni et al, "Signaling Through Zap-70 is Required for CXCL12-mediated T-cell Transendothelial Migration," *Blood,* 99:3111-3118, 2002. ZAP-70 is considered to be a prognostic indicator in B-cell chronic lymphocytic leukemia. See F. Bosch, "ZAP-70 Expression in CLL: a New Parameter for an Old Disease," *Haematologica,* 7:724-726, July, 2003; J. Orchard, "ZAP-70 Expression and Prognosis in Chronic Lymphocytic Leukemia," *Lancet,* 363:105-111, 2004; A. Wiestner, "Towards Molecular Diagnosis and Targeted Therapy of Lymphoid Malignancies," *Semin. Hematol.,* 40:296-307, Oct., 2003; J. Durig, "ZAP-70 Expression is a Prognostic Factor in Chronic Lymphocytic Leukemia," *Leukemia,* 17:2426-2434, Dec., 2003; M. Crespo, "ZAP-70 Expression as a Surrogate for Immunoglobulin-variable-region Mutations in Chronic Lymphocytic Leukemia," *N. Engl. J. Med.,* 348:1764-1775, May, 2003; and A. Weistner, "ZAP-70 Expression Identifies a Chronic Lymphocytic Leukemia Subtype with Unmutated Immunoglobulin Genes, Inferior Clinical Outcome, and Distinct Gene Expression Profile," *Blood,* 101:4944-4951, June, 2003.

FIG. 18 and Table 5 of our aforesaid patent application contain experimental data which shows that ZAP-70 was found to be present in SW480E cells, which are metastasizing, while little or none was found in the already metastasized cells, SW620, and none was found in SW480R cells, which are nonmetastasizing, thus showing experimentally that the presence of ZAP-70 in carcinoma cells may be a good predictor of metastasis.

SYKB is also known as SYK70, the 70-kDa isoform of the protein SYK. In a test the results of which are shown in Table 5 of our aforesaid patent application, SYKB was found in moderate amount in the SW480E (metastasizing) cell line, and none was found in the SW480R (non-metastasizing) cell line.

Table 3 of our aforesaid patent application contains data from experiments with Wistar Furth rats which shows that all of those breast cancer tumors (MT-449, MT-450, SMT-2A, and TMT-081) which were found to have cells expressing either CD4 or CD8 were metastasizing while all 6 tumors in which no CD4 or CD8 was found were nonmetastasizing. This data thus show experimentally that the presence of CD4 or CD8 in carcinoma cells may be a good predictor of metastasis.

In another test discussed in our aforesaid patent application (Table 6 thereof), with only one exception for one non-metastasizing tumor wherein the presence of CD8 was positive, CD3 and CD8 were not detected in any of the other twelve non-metastasizing breast tumors, CD3 was found in all of seven metastasizing breast tumors, and CD8 was found in five of the seven metastasizing breast tumors.

Table 6 of our aforesaid patent application shows the presence or absence of finding of the T-cell products CD3, CD4, and CD8 in fresh human breast cancer cells 13 of which had no lymph node involvement and were nonmetastasizing and 7 of which had lymph node involvement and were metastasizing. As seen in Table 6, with only an exception for one non-metastasizing tumor wherein the presence of CD8 was positive and the presence of CD4 was borderline, none of the T-cell products CD3, CD4, and CD8 was detected in any of the other 12 nonmetastasizing tumors and one or more of the T-cell products CD3, CD4, and CD8 was detected in each of the 7 metastasizing tumors.

The above findings clearly show that the detection of the presence of certain T-cell associated products including, but not limited to, CD3, CD4, CD8, SYKB, and ZAP-70 in a solid, non-lymphoid primary tumor may be a predictor of metastasis and that their absence (non-detection) may be a predictor of nonmetastasis.

As previously discussed, we have observed in numerous tests that rat mammary tumors with lymphotropic metastatic potential are non-tumorigenic in nude mice but the cells thereof were revivable (can be resuscitated) with the suppression of NK activity in the host mice while non-metastasizing control tumors were readily tumorigenic. It is therefore our belief, although we do not wish to be bound by theory here or elsewhere in this specification, that the tumorigenic cells are non-metastatic while the non-tumorigenic cells are metastatic. Accordingly, based on the above-discussed testing for lymphoid gene products and taking further into consideration the migratory nature of T-cells which contain lymphoid gene products, it is our further belief that lymphoid gene products or T-cell surface markers (including, but not limited to CD3, CD4, CD8, SYKB, and ZAP-70), especially collectively, may serve as indicators for metastatic potential.

Thus, in accordance with a preferred embodiment of the present invention, after a non-tumorigenic cell line has been developed to a desired purity, its cells are preferably tested for the presence of one or more lymphoid gene products to confirm that the cells of the cell line have lymphotropic metastatic potential.

Since, as previously discussed, NK-sensitive cells can be caused to metastasize in NK-deficient SCID mice, such a mouse may serve as a means for testing various potential anti-metastatic or otherwise anti-cancer agents. Thus, in accordance with a preferred embodiment of the present invention, in order to test potential treatments of a carcinoma (which may be obtained from a patient's tumor), a cell line of NK-sensitive cells is obtained as previously discussed, NK-sensitive cells of the cell line are injected subcutaneously into a SCID mouse or other SCID animal, and, after waiting a suitable period of time for lymph node metastasis to occur, testing a potential anti-metastasis or other anti-carcinoma agent on the SCID mouse.

By separating those cells (non-tumorigenic) which remain dormant under the influence of NK cells in a nude mouse, the present invention provides a new tool for studying cancer dormancy. This also allows the monitoring of a patient's NK status, i.e., by measuring CD56, a marker for NK cells, or other products of NK cells, after removal of a tumor as a means of monitoring dormancy status of metastatic cells during appropriate treatment. We believe the receptors on metastatic carcinoma cells for NK products such as, for example, CD95, CD95L, CD40, CD40L, and the interferon (INF) gamma receptor may be suitable markers therefor, and that perhaps interferon (INF) gamma may be a suitable treatment for carcinoma by maintaining dormancy of NK-sensitive (metastatic) cells.

As discussed above, there is provided, in accordance with a preferred embodiment of the present invention, a means using lymphoid gene products (T-lymphocyte and B cell-derived markers) for testing cell lines developed in accordance with the present invention to confirm that they have (or do not have) lymphotropic metastatic potential. Moreover, as carcinoma cells develop, they seem to acquire characteristics and markers of T and B cells, and that T and B cell-associated markers may accordingly be predictive of metastasis and lead to development of innovative cancer treatments.

By developing carcinoma cell lines in accordance with the present invention which are non-tumorigenic in nude mice, which we believe to have lymphotropic metastatic potential, research can then be conducted on cells which are truly metastatic, thus opening up a new and promising paradigm for human cancer research.

It should be understood that, while the present invention has been described in detail herein, the invention can be embodied otherwise without departing from the principles thereof, and such other embodiments are meant to come within the scope of the present invention as defined by the appended claims.

What is claimed is:

1. A method of separating tumor cells with lymphotropic metastatic potential from tumor cells without lymphotropic metastatic potential in a human carcinoma comprising the steps of
   a) transplanting cells of the carcinoma at a transplant site in each of a plurality of T-lymphocyte deficient environments which are adapted to suppress tumor growth of NK-sensitive cells;
   b) waiting a period of time after the cells are transplanted to determine whether a palpable tumor develops at the transplant site of at least one of the environments;
   c) alter waiting the period of time, treating with antibodies to NK cells at least one of the environments which does not develop a palpable tumor at the transplant site to overcome tumor growth suppression of NK-sensitive tumor cells in the treated environment; and
   d) harvesting tumor-forming cells at the transplant site of the treated environment to obtain a cell line of cells with lymphotropic metastatic potential.

2. A method according to claim 1 further comprising selecting the environments to be athymic animals.

3. A method according to claim 1 wherein the step of transplanting cells includes limiting the number of cells being transplanted in each of the environments to prevent overwhelming of the NK cells in the environments respectively, the method further comprising harvesting tumor-forming cells at the transplant site of at least one of the environments which, without the treatment thereof, develops a palpable tumor to obtain a cell line of cells without lymphotropic metastatic potential.

4. A method according to claim 1 further comprising testing cells of the cell line for the presence of one or more lymphoid gene products to confirm that the cells of the cell line have lymphotropic metastatic potential.

5. A method according to claim 1 further comprising cultivating cells of the cell line in vitro, and repeating steps a to d to obtain a more pure cell line of cells with lymphotropic metastatic potential.

6. A method of separating tumor cells with lymphotropic metastatic potential from tumor cells without lymphotropic metastatic potential in a human carcinoma comprising the steps of:
   a) transplanting cells of the carcinoma at a transplant site in each of a plurality of fresh athymic animals;
   b) waiting a period of time after the cells are transplanted to determine whether a palpable tumor develops at the transplant site of at least one of the athymic animals;
   c) after waiting the period of time, treating with antibodies to NK cells at least one of the athymic animals which does not develop a palpable tumor at the transplant site to suppress anti-tumor activity of natural kilter cells in the treated athymic animal; and
   d) harvesting tumor-forming cells at the transplant site of the treated athymic animal to obtain a cell line of cells with lymphotropic metastatic potential.

7. A method according to claim 6 further comprising testing cells of the cell line for the presence of one or more lymphoid gene products to confirm that the cells of the cell line have lymphotropic metastatic potential.

8. A method according to claim 1 further comprising injecting cells of the cell line into at least one SCID animal, and testing a potential anti-cancer agent on the injected SCID animal.

9. A method according to claim 6 further comprising cultivating cells of the cell line in vitro.

10. A method according to claim 9 further comprising transplanting at least some of the cultivated cells of the cell line in at least one other fresh athymic animal, confirming, after waiting a period of time after the transplanting in the at least one other athymic animal, no development of a palpable tumor at the transplant site thereof, treating with antibodies to NK cells the athymic confirmed other animal to suppress anti-tumor activity of natural killer cells in the treated athymic confirmed other animal; and harvesting tumor-forming cells at the transplant site of the treated athymic confirmed other animal to obtain a more pure cell line of cells with lymphotropic metastatic potential.

11. A method according to claim 10 further comprising repeating the steps of claims 9 and 10 with each transplantation being in a fresh athymic animal and with each cultivation being of the most recently harvested cells of the cell line, until a desired purity of the cell line is obtained.

12. A method according to claim 6 further comprising selecting the athymic animals to be athymic mice.

13. A method of separating tumor cells with lymphotropic metastatic potential from tumor cells without lymphotropic metastatic potential in a human carcinoma comprising the steps of:
 a) transplanting cells of the carcinoma at a transplant site in each of a plurality of fresh athymic animals, including limiting the number of cells being transplanted in each of the fresh athymic animals to prevent overwhelming of NK cells in the fresh athymic animals respectively;
 b) waiting a period of time after the cells are transplanted to determine whether a palpable tumor develops at the transplant site of at least one of the athymic animals;
 c) after waiting the period of time, harvesting tumor-forming cells at the transplant site of at least one of the athymic animals to obtain a first cell line of cells without lymphotropic metastatic potential;
 d) after waiting the period of time, treating with antibodies to NK cells at least one of the athymic animals which does not develop a palpable tumor at the transplant site to suppress anti-tumor activity of natural killer cells in the treated athymic animal; and
 e) harvesting tumor-forming cells at the transplant site of the treated athymic animal to obtain a second cell line of cells with lymphotropic metastatic potential.

14. A method according to claim 1 further comprising testing cells of each of the cell lines for the presence of one or more lymphoid gene products to confirm that the cell line of cells without lymphotropic metastatic potential does not have lymphotropic metastatic potential and that the cell line of cells with lymphotropic metastatic potential has lymphotropic metastatic potential.

15. A method according to claim 13 further comprising cultivating cells of the first and second cell lines separately in vitro.

16. A method according to claim 15 further comprising transplanting at least some of the cultivated cells of the first cell line in at least one second fresh athymic animal, including limiting the number of cells being transplanted in the at least one second fresh athymic animal to prevent overwhelming of the NK cells in the at least one second fresh athymic animal, and harvesting, after waiting a period of time after transplanting in the at least one second athymic animal, tumor-forming cells at the transplant site thereof to obtain a more pure first cell line of cells without lymphotropic metastatic potential.

17. A method according to claim 16 further comprising transplanting at least some of the cultivated cells of the second cell line in at least one third athymic animal, confirming, after waiting a period of time after transplanting in the at least one third athymic animal, no development of a palpable tumor at the transplant site thereof, treating with antibodies to NK cells the athymic confirmed third animal, to suppress anti-tumor activity of natural killer cells in the treated athymic confirmed third animal; and harvesting tumor-forming cells at the transplant site of the treated athymic confirmed third animal to obtain a more pure second cell line of cells with lymphotropic metastatic potential.

18. A method according to claim 17 further comprising repeating the steps of claims 15, 16, and 17 with each transplantation being in a fresh athymic animal and with each cultivation being of the most recently harvested cells of the respective cell line, until first and second cell lines of a desired purity are obtained.

19. A method according to claim 15 further comprising transplanting at least some of the cultivated cells of the second cell line in at least one other athymic animal, confirming, after waiting a period of time after transplanting in the at least one other athymic animal, no development of a palpable tumor at the transplant site thereof, treating with antibodies to NK cells the athymic confirmed other animal to suppress anti-tumor activity of natural killer cells in the treated athymic confirmed other animal; and harvesting tumor-forming cells at the transplant site of the treated athymic confirmed other animal to obtain a more pure second cell line of cells with lymphotropic metastatic potential.

20. A method according to claim 13 further comprising selecting the athymic animals to be athymic mice, and wherein the step of transplanting cells includes transplanting about 2 million of the cells in each of the athymic mice.

* * * * *